(12) United States Patent
Trummer et al.

(10) Patent No.: US 8,877,332 B2
(45) Date of Patent: Nov. 4, 2014

(54) USE OF A MIXTURE COMPRISING SPHERICAL METAL PARTICLES AND METAL FLAKES AS LASER-MARKING OR LASER-WELDABILITY AGENTS AND LASER MARKABLE AND/OR LASER WELDABLE PLASTIC

(75) Inventors: Stefan Trummer, Nürnberg (DE); Martin Schaal, Hohenstadt (DE); Marco Greb, Nürnberg (DE)

(73) Assignee: Eckart GmbH (DE)

( * ) Notice: Subject to any disclaimer, the term of this patent is extended or adjusted under 35 U.S.C. 154(b) by 479 days.

(21) Appl. No.: 12/593,098

(22) PCT Filed: Nov. 19, 2008

(86) PCT No.: PCT/EP2008/009767
§ 371 (c)(1),
(2), (4) Date: Mar. 8, 2010

(87) PCT Pub. No.: WO2009/068207
PCT Pub. Date: Jun. 4, 2009

(65) Prior Publication Data
US 2010/0196698 A1  Aug. 5, 2010

(30) Foreign Application Priority Data
Nov. 30, 2007 (EP) .................................. 07023229

(51) Int. Cl.
| | | |
|---|---|---|
| B32B 27/04 | (2006.01) | |
| C08K 7/18 | (2006.01) | |
| C08K 9/06 | (2006.01) | |
| B41M 5/26 | (2006.01) | |
| B29C 65/00 | (2006.01) | |
| B29K 305/00 | (2006.01) | |
| B29C 65/16 | (2006.01) | |
| B29C 35/08 | (2006.01) | |
| C08L 21/00 | (2006.01) | |
| B29K 1/00 | (2006.01) | |
| G01N 15/02 | (2006.01) | |
| B29K 105/16 | (2006.01) | |

(52) U.S. Cl.
CPC ............ B41M 5/267 (2013.01); B29K 2305/00 (2013.01); B29C 65/1619 (2013.01); B29C 2035/0822 (2013.01); B29C 65/1606 (2013.01); B29C 65/1674 (2013.01); B29C 65/1677 (2013.01); C08L 21/00 (2013.01); B29K 2001/14 (2013.01); B29C 66/71 (2013.01); B29C 2035/0827 (2013.01); G01N 15/0205 (2013.01); B29K 2105/16 (2013.01); B29K 2001/12 (2013.01)
USPC .......................................... 428/328; 428/546

(58) Field of Classification Search
USPC .................................................. 428/328, 546
See application file for complete search history.

(56) References Cited

U.S. PATENT DOCUMENTS

| | | |
|---|---|---|
| 2,071,250 A | 2/1937 | Carothers |
| 2,071,251 A | 2/1937 | Carothers |
| 2,130,523 A | 9/1938 | Carothers |
| 2,130,948 A | 9/1938 | Carothers |
| 2,241,322 A | 5/1941 | Hanford |
| 2,312,966 A | 3/1943 | Hanford |
| 2,512,606 A | 6/1950 | Bolton et al. |
| 3,055,859 A | 9/1962 | Vollmert |
| 3,393,210 A | 7/1968 | Speck |
| 3,530,094 A | 9/1970 | Schnell et al. |
| 3,535,280 A | 10/1970 | Schnell et al. |
| 4,224,419 A | 9/1980 | Swoboda et al. |
| 4,537,949 A | 8/1985 | Schmidt et al. |
| 4,540,772 A | 9/1985 | Pipper et al. |
| 4,634,734 A | 1/1987 | Hambrecht et al. |
| 4,957,965 A | 9/1990 | Taubitz et al. |
| 4,970,255 A | 11/1990 | Reimann et al. |
| 6,323,279 B1 | 11/2001 | Guntherberg et al. |
| 6,545,065 B2 | 4/2003 | Solms et al. |
| 6,693,657 B2 | 2/2004 | Carroll, Jr. et al. |
| 6,727,308 B2 | 4/2004 | Kniess et al. |
| 6,776,835 B2 | 8/2004 | Andes et al. |
| 7,674,845 B2 | 3/2010 | Van Duijnhoven et al. |
| 8,318,262 B2 | 11/2012 | Greb et al. |

(Continued)

FOREIGN PATENT DOCUMENTS

| | | |
|---|---|---|
| CA | 2294235 | 12/1998 |
| DE | 1 495 730 | 4/1969 |
| DE | 1 300 266 | 4/1970 |
| DE | 196 32 675 A1 | 2/1998 |
| DE | 197 26 136 | 12/1998 |
| DE | 197 28 629 | 1/1999 |
| DE | 198 10 952 A1 | 6/1999 |
| DE | 10 2004 053 376 A1 | 6/2005 |
| DE | 10 2004 045 305 A1 | 3/2006 |

(Continued)

OTHER PUBLICATIONS

International Search Report dated Apr. 3, 2009, issued in corresponding international application No. PCT/EP2008/009767.
Notice of Reasons for Rejection dated Dec. 25, 2012 in corresponding Japanese Patent Application No. 2010-535270 (with English language translation).

Primary Examiner — Samir Shah
(74) Attorney, Agent, or Firm — Ostrolenk Faber LLP

(57) ABSTRACT

The use of a mixture with spherical metal particles and metal flakes as a laser marking or laser weldability agent in a plastic, wherein the particle size distribution of the spherical metal particles and metal flakes, as determined with laser granulometry, in the form of the volume-averaged cumulative undersize particle size distribution, has a $D_{mixture,\ 90}$ value of <100 μm and a $D_{mixture,\ 50}$ <60 μm. Further, a masterbatch comprising a mixture with spherical metal particles and metal flakes also can be used. Additionally, the present subject matter may further relate to a laser markable and/or a laser weldable plastic comprising a mixture with spherical metal particles and metal flakes.

12 Claims, No Drawings

(56) References Cited

U.S. PATENT DOCUMENTS

| | | |
|---|---|---|
| 2002/0107305 A1 | 8/2002 | Edler |
| 2004/0013969 A1 | 1/2004 | Delp et al. |
| 2006/0202173 A1* | 9/2006 | Konno et al. ............... 252/512 |
| 2006/0216441 A1 | 9/2006 | Schubel et al. |
| 2006/0276565 A1 | 12/2006 | Polta et al. |
| 2007/0080146 A1* | 4/2007 | Stockum et al. ........... 219/121.6 |
| 2007/0173581 A1 | 7/2007 | Hager et al. |
| 2008/0001692 A1 | 1/2008 | Miyahara et al. |
| 2009/0104447 A1* | 4/2009 | Kita et al. .................... 428/412 |
| 2010/0009171 A1* | 1/2010 | Greb et al. ................... 428/328 |

FOREIGN PATENT DOCUMENTS

| | | |
|---|---|---|
| DE | 10 2005 011 180 A1 | 9/2006 |
| DE | 102006062269 * | 6/2008 |
| EP | 38 094 | 3/1981 |
| EP | 38 582 | 3/1981 |
| EP | 39 524 | 3/1981 |
| EP | 99 532 | 4/1983 |
| EP | 129 195 | 6/1984 |
| EP | 129 196 | 6/1984 |
| EP | 135 130 | 8/1984 |
| EP | 0 126 787 A | 12/1984 |
| EP | 299 444 | 7/1988 |
| EP | 302 485 | 8/1988 |
| EP | 113 112 | 6/1993 |
| EP | 1 145 864 A | 10/2001 |
| EP | 1 215 233 A | 6/2002 |
| EP | 1 279 517 A | 1/2003 |
| JP | 11070734 | 3/1999 |
| JP | 2001-505233 | 4/2001 |
| JP | 2002-522618 | 7/2002 |
| JP | 2005-162913 | 6/2005 |
| JP | 2005-290087 | 10/2005 |
| JP | 2006-509099 | 3/2006 |
| JP | 2006-098969 | 4/2006 |
| JP | 2010-513609 | 4/2010 |
| WO | WO 02/055287 A1 | 7/2002 |
| WO | WO 2004/045857 A2 | 6/2004 |
| WO | WO 2005/047009 | 5/2005 |
| WO | WO 2005/084956 | 9/2005 |
| WO | WO 2006/029677 | 3/2006 |
| WO | WO 2007/062785 A2 | 6/2007 |
| WO | WO2007105741 * | 9/2007 |

* cited by examiner

USE OF A MIXTURE COMPRISING SPHERICAL METAL PARTICLES AND METAL FLAKES AS LASER-MARKING OR LASER-WELDABILITY AGENTS AND LASER MARKABLE AND/OR LASER WELDABLE PLASTIC

CROSS REFERENCE TO RELATED APPLICATIONS

The present application is a 35 U.S.C. §371 National Phase conversion of PCT/EP2008/009767, filed Nov. 19, 2008, which claims benefit of European Application No. 07023229.3, filed Nov. 30, 2008, the disclosure of which is incorporated herein by reference. The PCT International Application was published in the German language.

TECHNICAL FIELD

The invention relates to the use of a mixture with spherical metal particles and metal flakes as an additive for laser marking and/or laser welding of plastics. The invention further relates to a laser-markable and/or laser-weldable plastic which comprises a mixture with spherical metal particles and metal flakes.

BACKGROUND of the INVENTION

The marking of plastics by laser and the welding of plastics parts by means of laser energy are known per se. Both are brought about as a result of absorption of the laser energy in the plastics material, either directly, by interaction with the polymer, or indirectly, with a laser-sensitive agent added to the plastics material. The laser-sensitive agent may be an organic dye or a pigment which, by absorbing the laser energy, produces a visible local change in color in the plastic. It may also be a compound which, when irradiated with laser light, is converted from an invisible, colorless form into a visible form. In the case of laser welding, the heating of the plastics materials as a result of absorption of the laser energy in the joining region is so great that the material melts and the two parts weld to one another.

The marking of production goods is becoming increasingly important in virtually all branches of industry as part of the general rationalization measures. Thus, for instance, there is a need to apply production data, batch numbers, expiration dates, product IDs, bar codes, corporate logos, etc. Set against conventional marking techniques such as printing, embossing, stamping, and labeling, laser marking is significantly quicker, on account of its contactless operation, and is more precise and is also unproblematic to apply to nonplanar surfaces. Since the laser markings are generated beneath the surface in the material, they are durable, robust and substantially more secure with respect to removal, alteration or even counterfeiting. Contact with other media, such as in the case of containers for liquids, and closures, is likewise uncritical for this reason—on the assumption, of course, that the plastics matrix is stable. Security and durability of production IDs, and also freedom from contamination, are extremely important in the case, for instance, of packaging of pharmaceuticals, comestibles, and beverages.

Laser marking technology has proven very suitable in particular in connection with the marking of plastics. To be able to carry out efficient marking of plastics it is necessary to generate sufficient interaction between the plastic to be marked and the laser light. Here, firstly, it must be borne in mind that the energy introduced into the plastics should not be too high, since it may destroy the plastics article or its texture. Secondly, the laser beam must not pass through the plastic without significant interaction, since in that case the plastic cannot be marked.

In order to increase the interaction of the laser beam with the plastic, plastics are used in which absorption agents, also referred to as absorbers, have been incorporated. These absorbers may be, for example, laser-markable polymers or else pearlescent pigments and metallic effect pigments.

In the case of pearlescent pigments and metallic effect pigments, the irradiation of laser light results in heating of these pigments. In the immediate environment of the pearlescent pigments and of the metallic effect pigments, there is then a thermal change in the plastic, e.g., a carbonization or a foaming of the plastic, thereby allowing marking or identification of the plastics article.

DE 197 26 136 A1 discloses the use of laser-markable polymers in the form of microground particles having a size of 0.1 to 100 μm. A disadvantage of these laser-markable polymers is that they can melt during the processing of the plastics doped with the laser-markable polymers. It is therefore necessary for the melting ranges of the incorporated laser-markable polymer and of the plastics system used to be harmonized with one another.

DE 198 10 952 A1 discloses the use of pearlescent pigments or metallic luster pigments as absorbers in plastics.

WO 2004/045857 A2 describes a laser marking process using an ink, possibly comprising pearlescent pigments and metallic effect pigments as laser-sensitive materials.

From WO 2007/062785 A1 is a laser-transferable security feature for which laser-sensitive materials can be used that include pearlescent pigments or metallic effect pigments or metal powders, including mixtures of these. Pearlescent pigments are particularly preferred here.

A disadvantage of the use of pearlescent pigments or metallic luster pigments or metallic effect pigments is that satisfactory contrast after laser marking is achievable only with a high level of pigmentation. The level of concentration that must be chosen for the quantity of pigment is so high that it automatically entails coloring of the plastic with the pearlescent or metallic effect pigments.

Accordingly, with the exclusive use of pearlescent pigments and/or metallic effect pigments, it is not possible satisfactorily to achieve high-contrast laser marking without appreciable coloring in the case of pearlescent pigments (pearl luster effect) or without appreciable metallic coloration in the case of metallic luster or metallic effect pigments.

Moreover, the plateletlike structure of the pearlescent pigments or of the metallic luster or metallic effect pigments, at the concentrations that need to be used, has the deleterious effect that the pigments, owing to their platelet structure, undergo orientation in the laminar flow that is an inevitable corollary of the operation of injection molding of the plastics mass, and this leads to flow lines or streaks in the plastics article produced.

To obtain a desired contrast in the laser marking of plastics, EP 1 145 864 A1 teaches using a mixture of metal powder and/or semimetal powder and of an effect pigment or two or more effect pigments based on phyllosilicates. Here again there is visible coloration of the plastic, which is unwanted for clear and transparent plastics. Moreover, the pearlescent pigments likewise deleteriously produce streaks or flow lines in the plastics articles produced.

DE 10 2004 053 376 A1 discloses colored laser markings and laser inscriptions on plastics that are based on the welding of a polymeric inscription medium to the plastics surface. The energy absorbers suitable for marking that are mentioned in this specification include spherical metal powders, among other absorbers. No details, however, are given concerning the size of the metal powders.

Among the absorbers for masking laser beams that are described in JP 11070734 AA are metal powders. In this case the metal powders are used in a concentration of 5% to 90%, based on the shielding layer. At these very high concentrations, hazing of the medium occurs inevitably.

In accordance with the teaching of DE 10 2004 045 305 A1, the problem that exists in the prior art of the absorbers sustainedly coloring the plastics to be inscribed can be eliminated by incorporating a boride compound, preferably lanthanum hexaboride, into the plastics material. A disadvantage is that these boride compounds, especially lanthanum hexaboride constitute a significant cost factor. Consequently these boride compounds are not suitable as a laser marking agent for widespread use.

In order to allow marking of transparent plastics materials without coloration, use is made, in accordance with the teaching of U.S. Pat. No. 6,693,657 B2 and also of WO 2005/047009, of a laser marking agent which comprises a mixture of antimony oxide and tin oxide. WO 2005/084956 describes high-transparency plastics materials which are laser-markable and/or laser-weldable by means of nanoscale indium-tin oxide or antimony tin oxide particles. A disadvantage is that, like any other antimony compound, antimony oxide is highly toxic. Consequently this laser marking agent poses, on the one hand, a considerable risk to environment and people, both in production and processing and in disposal, since, firstly, antimony or compounds containing antimony must be used and, lastly, the plastics articles which contain antimony and/or compounds containing antimony must be disposed of again.

WO 2002/055287 A1 describes a process for producing laser-welded composite moldings. It mentions metal flakes and metal powders as fillers. These fillers, however, are used at relatively high concentrations of 1% to 60% by weight, based on the plastics molding.

SUMMARY

It is an object of the present invention to provide a laser marking agent that allows marking of transparent plastics materials with effective contrast and with high efficiency. The efficiency is to be characterized in that the amounts of the laser marking agent that must be used are as small as possible. An effective contrast is preferably to be obtained without having to color the plastics materials automatically.

It is a further object of the invention to provide a toxicologically unobjectionable laser marking agent which is available inexpensively and in large quantities.

A further object is to provide a laser-markable and/or laser-weldable plastic with a laser marking agent that exhibits virtually no hazing or coloration as a result of the laser marking agent.

The object on which the invention is based is achieved through the use of a mixture with spherical metal particles and metal flakes as a laser marking agent in a plastic, wherein the particle size distribution of the spherical metal particles and of the metal flakes in the mixture, as determined by means of laser granulometry, in the form of the volume-averaged cumulative undersize particle size distribution, has a $D_{mixture,\ 90}$ value of <100 μm and a $D_{mixture,\ 50}$ value of <60 μm.

Preferred developments of the inventive use are specified in dependent claims 2 to 11.

The object on which the invention is based is also achieved through provision of a masterbatch, the masterbatch comprising the mixture with spherical metal particles and metal flakes, for use as claimed in claims 1 to 11, and also at least one dispersion carrier.

Preferred developments of the inventive masterbatch are specified in dependent claims 13 to 15.

The object of the invention is also achieved as well through the use of a masterbatch as claimed in any of claims 12 to 15 for producing a laser-markable and/or laser-weldable plastic.

The object of the invention is further achieved by provision of a laser-markable and/or laser-weldable plastic which comprises a mixture with spherical metal particles and metal flakes, for use as claimed in any of claims 1 to 11, or a masterbatch as claimed in any of claims 12 to 15.

Preferred developments of the inventive laser-markable and/or laser-weldable plastic are specified in dependent claims 18 to 25.

DETAILED DESCRIPTION

Laser granulometry is a laser diffraction method in which the size of the particles is determined from the diffraction of the laser light. Since the materials used are used preferably in the form of powders, it is preferred to carry out the laser diffraction method with the Helos instrument from Sympatec, Clausthal-Zellerfeld, Germany, in accordance with the manufacturer's instructions.

The particle size distribution of the metal flakes added proportionally to the spherical metal particles in this case preferably has a $D_{flake,\ 90}$ value <100 μm and a value of $D_{flake,\ 50}$ in the range from 1 μm to 60 μm; with particular preference the $D_{flake,\ 50}$ value is in the range from 2 μm to 40 μm.

In accordance with one preferred version of the invention the spherical metal particles and metal flakes are largely heavy metal free.

"Heavy metal free" for the purposes of the invention means that the percentage weight fraction of the heavy metals of the spherical metal particles and of the metal flakes independently of one another is below 0.5% by weight and preferably below 0.1% by weight. Heavy metals here are essentially toxicologically objectionable heavy metals such as lead, arsenic, antimony, mercury, bismuth, cobalt, indium, thallium, cadmium, etc. and mixtures thereof.

"Largely heavy metal free" in the sense of the invention means that the percentage weight fraction of the heavy metals of the spherical metal particles and of the metal flakes independently of one another can be up to a maximum of 1% by weight.

Metal powders are well established. Their uses include a starting material for the production of metallic effect pigments. Thus, for example, zinc powder is used as a corrosion pigment.

Metal flakes are customarily used as metallic effect pigments in application media such as paints, varnishes, printing inks, plastics, and cosmetics in order to generate an optical metallic effect. This refers customarily to the flop effect, metallic luster and brilliance, and also the high opacity. Thus, for example, aluminum flakes or bronze flakes are used in order to generate silver or gold effects, respectively, in paints.

Metal flakes for the purposes of the invention are platelet-shaped metallic particles which have a form factor of 2 to 1500 and preferably of 5 to 500. Form factor is the ratio of average particle size $D_{flake,\ 50}$ to average thickness. The terms "metal flakes" and "metallic effect pigments" are used interchangeably in the present text.

By spherical metal particles are meant, for the purposes of the invention, not necessarily an absolutely concentric three-dimensional structure.

Spherical metal particles for the purposes of the invention do not have the plateletlike form of effect pigments, such as pearlescent pigments or metallic effect pigments. The form factor of the spherical metal pigments is smaller than 2:1. The term "spherical form" for the purposes of the invention also refers, for example, to a form which has only an approximately spherical form, an ellipsoidal form, or is multifarious. A multifarious form is characterized in particular in that on a non-planar body there may be, on the surface, for example, dendritic projections. Moreover, the surface may also have been irregularly shaped. Spherical metal particles of this kind can be obtained, for example, by nozzle spraying or atomization of molten metal. They are produced commercially in large volumes and are available inexpensively, from Ecka Granulate (D-91235 Velden, Germany), for example.

It has emerged, completely surprisingly, that metal powders in the form of a mixture with spherical metal particles and metal flakes are outstandingly suitable as a laser marking additive. Besides the spherical metal particles and metal flakes, the mixture may also comprise further additives or adjuvants.

In accordance with one preferred development, the mixture to be used is composed of spherical metal particles and metal flakes.

Entirely surprising in this context is that a mixture of spherical metal particles and metal flakes allows high-contrast marking without necessarily transparent plastics materials having to be made hazy or colored.

The exclusive use of metal flakes has very deleterious consequences for the transparency of a plastic. Even in relatively low concentrations there may be severe clouding or metallic coloration, which in the sense of the stated object is regarded as disadvantageous.

It has emerged, surprisingly, that a mixture with or of spherical metal particles and metal flakes is outstanding suitable as a laser marking additive in plastics. The clouding of the plastics is in this case less pronounced than in the case of the exclusive use of metal flakes.

Without wishing to be tied by a theory in any form, it may be the case that metal flakes, on account of their platelet form, have a higher specific surface area than spherical metal particles of comparable size. This goes hand in hand with a greater efficiency in the absorption of laser radiation and also in the subsequent delivery of heat to the plastic. These properties are accompanied, however, likewise by a greater interaction with visible light, which is manifested ultimately in an increased clouding behavior.

In the case of a spherical form of the metal particles, in contradiction to the planar metallic effect pigments, incident light is not reflected in a directed way, and so is not perceived as a strongly reflecting pigment by a viewer. Advantageously, spherical metal particles have the capacity to absorb the irradiated laser light to a high degree, like metal flakes, and, accordingly, to convert it into heat.

Entirely surprisingly it has been found that, with relatively low proportions of the metal flakes in the mixture according to the invention, the advantageous properties of the metal flakes are effective without leading to excessive clouding in the visible region.

The heat absorption capacity of spherical metal particles and metal flakes is far more pronounced than in the case, for instance, of pearlescent pigments, and the mixture according to the invention can therefore be used at far lower concentrations.

In principle the spherical metal particles and metal flakes used for laser marking can have a wide particle size range. Preference, however, is given to using relatively small spherical metal particles and metal flakes. It has emerged, surprisingly, that the distinctness of image, and especially the dot precision, of the laser marking are better when using relatively small metal particles. The dot precision is impaired when even small amounts of excessively large spherical metal particles or metal flakes are present.

By dot precision is meant high resolution of the laser marking without large, disruptive scattered dots.

The improved dot precision and distinctness of image mean that the mixture for use in accordance with the invention, comprising or composed of spherical metal particles and metal flakes, can be employed with good results even at substantially increased write speeds.

Surprisingly it has emerged that, when a mixture comprising or composed of spherical metal particles and metal flakes is used, there is a synergistic effect: the dot precisions, contrasts, and laser markabilities to be obtained from the proportionally used spherical metal particles add with the two-dimensional efficiency that originates from the proportionally used metal flakes even at low concentrations and therefore without causing significant clouding of the medium.

As a result of this synergistic effect, the amount of material used can be additionally reduced in comparison to the exclusive use of the individual components—in other words, the mixture for use in accordance with the invention exhibits a heightened efficiency.

Metal particles such as spherical particles and metal flakes possess a particle size distribution which commonly has approximately the form of a log-normal distribution. The size distribution is customarily determined by means of laser granulometry.

In the case of this method it is possible to measure the metal particles in the form of a powder. The scattering of the irradiated laser light is detected in different spatial directions and is evaluated in accordance with the Fraunhofer diffraction theory, by means of the Windox software, version 5, release 5.1 that is used in conjunction with the Helos instrument from Sympatec, Germany, in accordance with the manufacturer's instructions. Arithmetically, the particles are treated as spheres. Consequently the diameters determined always relate to the equivalent sphere diameter, averaged over all spatial directions, independently of the actual form of the metal particles. The size distribution determined is that calculated in the form of a volume average (relative to the equivalent sphere diameter). This volume-averaged size distribution can be depicted inter alia as a cumulative undersize curve. The cumulative undersize curve in turn is usually characterized, simplifyingly, by means of defined characteristic values, examples being the $D_{50}$ or $D_{90}$ value. A $D_{90}$ value means that 90% of all of the particles lie below the stated value. Expressed alternatively, 10% of all the particles lie above the stated value. In the case of a $D_{50}$ value, 50% of all the particles lie above, and 50% of all the particles below, the stated value.

In the text below, the characteristics of the cumulative undersize curve of the size distribution of the spherical metal particles and metal flakes for use in accordance with the invention, in the mixture, are identified with the suffix or index "mixture". The suffix or index "particle" refers to the spherical metal particles, and the suffix or index "flake" to the metal flakes.

The mixtures for use in accordance with the invention have a particle size distribution with a $D_{mixture, 90}$ value of <100 μm and a $D_{mixture, 50}$ value <60 μm. With particular preference the mixtures used in accordance with the invention have a $D_{mixture,\ 50}$ value in the range from 0.5 to <45 μm.

In the case of excessively coarse mixtures with a particle size distribution having a $D_{mixture,\ 90}$ value of >100 μm, the desired contrast and in particular the dot precision of the laser marking are lacking and are very greatly adversely affected.

The same applies if, for example, the particle size distribution of the spherical metal particles or of the metal flakes has a $D_{mixture,\ 90}$ value of <100 μm and yet the $D_{mixture,\ 50}$ value is >60 μm. Spherical metal particles or metal flakes of such a kind possess a relatively low fine fraction and do not have the advantages described in this invention.

Preferably the $D_{mixture,\ 90}$ value is <70 μm. Associated herewith preferably are particle size distributions having a $D_{mixture,\ 50}$ value of <40 μm. With particular preference the mixtures used in accordance with the invention have a $D_{mixture,\ 50}$ value in the range from 0.6 to below 40 μm. When these relatively fine metal particles are used, the dot precision of the laser marking is further improved, since the dot precision is impaired even by small amounts of excessively large metal particles or flakes. Optically visible, disruptive particles occur in particular when coarse spherical metal particles or metal flakes are used.

In this context the metal flakes used in accordance with the invention preferably have a particle size distribution $D_{flake,\ 50}$ value in a range from 1 to 60 μm. With particular preference the metal flakes used in accordance with the invention have a $D_{flake,\ 50}$ value in the range from 2 to 40 μm.

In the case of the proportional use of coarse metal flakes having a $D_{flake,\ 50}$ value >60 μm, satisfactory dot precision is unobtainable.

Depending on the ratio of mixing of the two metallic pigment components to one another, the size distributions of the individual components may differ. Thus, in the case of a very small admixture of metal flakes, these may have a coarser structure than the spherical metal particles. Where similar amounts of both components are mixed, they ought also to resemble the size distributions accordingly.

A mixture of spherical metal particles and metal flakes that is intended for use in accordance with the invention is in this case composed preferably proportionally of a weight ratio of spherical metal particles to metal flakes of 500:1 to 1:1.

Above a weight ratio of 500:1 of spherical particles to metal flakes it may be the case that this mixture can no longer be distinguished from the exclusive use of spherical particles.

Above a weight ratio of 1:1 of metal flakes to spherical metal particles, such as with a weight ratio of 5:1, for example, it may be the case that the mixture can essentially no longer be distinguished from the exclusive use of metal flakes. In that case the clouding of the plastic that is achieved may be too high.

A preferred weight ratio of spherical metal particles to metal flakes is in the range from 300:1 to 1:1, more preferably from 250:1 to 1.5:1, and more preferably still from 100:1 to 2:1. Particular preference is additionally given to a ratio in the range from 50:1 to 2.5:1. A weight ratio of spherical metal particles to metal flakes in the range from 30:1 to 3:1 has also proven highly suitable.

As well as deficient dot precision, another observation, particularly in the case of large metal flakes, is the appearance of optical glitter effects. This is usually unwanted in the application and is considered disadvantageous for the invention. It is preferred in accordance with the invention to add metal flakes with a $D_{flake,\ 50}$ value <45 μm in order to reduce the incidence of disruptive, glittering coarse particles. The effect is reduced further as the particle size goes down, and so, additionally, it is preferred to use metal flakes having a $D_{flake,\ 50}$ value <35 μm and, with particular preference, metal flakes having a $D_{flake,\ 50}$ value <25 μm.

In the case of one preferred embodiment, the mixture comprising or composed of spherical metal particles and metal flakes has a particle size distribution having a $D_{mixture,\ 90}$ value of <65 μm. In this case the $D_{mixture,\ 50}$ value of the particle size distribution is preferably <35 μm. With particular preference the mixture for use in accordance with the invention, comprising or composed of spherical metal particles and metal flakes, has a $D_{mixture,\ 50}$ value in the range from 0.55 to <30 μm. Mixtures of this kind have a relatively high dot precision and an improved contrast.

Particular preference is given to using mixtures, used in accordance with the invention, having a particle size distribution with a $D_{mixture,\ 90}$ value of <50 μm. With further preference the $D_{mixture,\ 50}$ value of the particle size distribution is <20 μ. More preferably the mixtures used in accordance with the invention have a $D_{mixture,\ 50}$ value in the range from 0.6 to <20 μm. As fineness increases, i.e., as the particle size of the spherical metal particles and/or of the metal flakes goes down, it is possible that the distinctness of image and the dot precision of the image or identification applied by laser marking will be increased still further.

Particularly fine sizes of spherical metal particles and/or metal flakes produce a decidedly high distinctness of image, dot precision, and contrast on laser marking.

It is supposed that, as a result of the use of fine spherical metal particles and metal flakes, on the basis of their high specific surface area, the absorption of laser light and, subsequently, the delivery of energy to the environment of the metal particle or metal flake takes place in a particularly defined, locally narrowly limited way. Accordingly the laser markings on correspondingly pigmented plastics exhibit the advantages stated.

In one especially preferred embodiment, mixtures used in accordance with the invention are used that have a particle size distribution with a $D_{mixture,\ 90}$ value of <25 μm. In the case of these spherical metal particles the $D_{mixture,\ 50}$ value of the particle size distribution is preferably <11 μm. With particular preference the spherical metal particles in the mixture have a $D_{mixture,\ 50}$ value in the range from 0.65 to <11 μm.

In one preferred version of the invention the particle size distribution of the metal flakes as determined by means of laser granulometry, in the form of the volume-averaged cumulative undersize particle size distribution, has a $D_{flake,\ 50}$ from a range from 1 to 60 μm.

With these very fine spherical metal particles and metal flakes it has surprisingly been found that laser markings of high contrast and dot precision can be obtained at very high laser write speeds. The write speeds of the laser range from 10 to about 20 000 mm/s, preferably from 50 to 15.000 mm/s, more preferably from 100 to 11.000 mm/s, and very preferably from 200 to 10.000 mm/s. The write speed that is achievable in each specific case is dependent here on a large number of parameters, but particularly on the laser power and the pulse frequency. This brings considerable time advantages with it in respect of the throughput rates in the laser marking of objects.

In a further preferred embodiment the spherical metal particles in the mixture have a particle size distribution with smaller characteristic values, $D_{50}$ or $D_{90}$ values, for example, than the corresponding characteristic values of the metal flakes in the mixture.

The ratio of the $D_{50}$ values of spherical metal particles to metal flakes in the mixture according to the invention is preferably less than 1.0, more preferably less than 0.75, more preferably still less than 0.5, and very preferably less than 0.4.

In accordance with a further preferred embodiment of the invention the spherical metal particles and metal flakes that are used in the mixture according to the invention have a natural metal oxide content of not more than 15% by weight, based on the total weight of the spherical metal particles and metal flakes. It is further preferred for the natural metal oxide content to be not more than 10% by weight, and more preferably not more than 5% by weight. A natural metal oxide content of about 0.3% to 6% by weight and more preferably of 0.4% to 1.5% by weight has proven very suitable.

The low natural metal oxide contents are advantageous for the rapid absorption of energy from the irradiated laser beam by the spherical metal particles and metal flakes. The lower limit of 0.3% by weight natural metal oxide content is dictated by the oxide layer that naturally forms on the metals.

The natural metal oxide content of the spherical metal particles and metal flakes may involve a metal oxide layer formed superficially. By way of example, aluminum particles have a thin layer of aluminum oxide on the surface.

The spherical metal particles and the metal flakes of the mixture according to the invention thus are composed preferably to an extent of about 80% by weight, more preferably to an extent of about 85% by weight, with further preference to an extent of about 90% by weight, and even more preferably to an extent of about 95% by weight, of metal. The metal particles are preferably composed to an extent of 98.5% to 99.6% by weight of metal, these figures relating in each case to the total weight of metal and natural metal oxide.

A natural metal oxide content for the purposes of the invention means the amount of metal oxide which forms on a metal by oxidation of the metal surface.

The natural metal oxide is to be distinguished from the metal oxide which is applied in a separate coating process, as described later on below. This additionally applied metal oxide layer is an inorganic metal oxide layer in which the metal is different from the metal of the coated spherical metal particle or metal flake. Generally speaking, this inorganic metal oxide layer is a silicon oxide, titanium oxide and/or aluminum oxide layer.

The spherical metal particles and metal flakes used in the mixture according to the invention, independently of one another, preferably comprise or consist of metals selected from the group consisting of aluminum, copper, silver, gold, zinc, tin, iron, titanium, vanadium, magnesium, tungsten, and alloys thereof. An alloy need not necessarily be composed exclusively of the aforementioned metals. It is also possible for there to be further metals alloyed with the aforementioned metals or alloys thereof, including metals in the form of impurities, for example.

Aluminum, silver, copper, zinc, and iron have proven very suitable metals. A plastic which comprises these metals only at very low concentrations, as for example in a range of 0.0005% or 0.001% by weight, based in each case on the total weight of the plastic and also of the metals in particle form and flake form, can be marked very effectively using a laser. One suitable alloy is brass, for example.

In view of the microscale particle size distribution of the metal particles and metal flakes, the laser marking agent of the invention exhibits an extremely high dot precision.

Following irradiation of a laser beam into a plastic which comprises the laser marking agent for use in accordance with the invention there is selective heating of the microscale spherical metal particles and metal flakes, and, subsequently, the transfer of the heat to the surrounding plastic. The heat that is given off then brings about thermally induced polymer breakdown, leading to carbonization and/or to foaming of the polymers surrounding the spherical metal particles and metal flakes in the plastics matrix. Carbonization and/or foaming occurs depending on the nature of the polymer used and/or depending on the energy input by the laser beam.

Carbonization leads to blackening; foaming leads to a lightening in color, which can lead to up to a kind of whitening.

In the majority of cases the desire is for a distinct contrast to the unmarked plastic, something which is best achievable by carbonization.

In further embodiments, the change in the plastic that is brought about by the thermally induced polymer breakdown may be so small that it cannot be perceived, or not significantly, with the human eye. Marks of this kind can, however, be detected by special read devices. Accordingly such substantially invisible laser markings may find use, for example, for security markings or on CDs.

Further embodiments envision deliberate discoloration of the plastic by admixing of a colorant which undergoes targeted degradation with the irradiated laser light. For instance, this colorant may decompose under the action of the laser light, causing the plastic to become less colored in addition to the blackening or lightening. If the plastic comprises further colorants which are not degraded by the laser light, the plastic, following irradiation of the laser light and decomposition of the colorants sensitive to laser light, may take on the inherent color of the colorants which are not degradable by laser light.

Since the carbonization and/or foaming takes place only locally around the microscale metal particles, marking can be carried out with high dot precision. A high distinctness of image is manifested by facts which include the fact that a line is perceived not as a collection of individual dots but instead as a continuous straight line, which is composed of a multiplicity of small dots that the human eye is unable to resolve.

It has therefore emerged as being extremely surprising that—although the interaction of the spherical metal particles and metal flakes at low concentrations with visible light is not strong enough to cause graying (clouding) of a plastics material—the interaction with irradiated laser light is nevertheless sufficient to generate the desired carbonization and/or foaming of the polymer matrix surrounding the metal particles and hence to provide the plastics article with a high-contrast identification or marking.

On account of their very high absorption capacities for electromagnetic radiation from the UV through to the IR range, and also on account of their excellent thermal conductivity, the microscale spherical metal particles and metal flakes of the mixture according to the invention are especially suitable as laser marking agents and/or laser weldability agents. In their activity in these respects they exceed conventional metal-oxide particles.

The mixture of spherical metal particles and metal flakes can be added in the form of a powder to the plastic. More advantageous, however, is the addition of the mixture for use in accordance with the invention in the form of a concentrate or masterbatch. It has emerged that concentrates or masterbatches considerably facilitate the incorporability of the mixture of spherical metal particles and metal flakes into plastics.

A masterbatch for the purposes of the present invention comprises a mixture of spherical metal particles and metal flakes and at least one dispersion carrier.

In the masterbatch the amount of spherical metal particles and metal flakes is in a range from 0.001% to 99.9% by weight, based on the total weight of the masterbatch. Preferably the amount of spherical metal particles and metal flakes in the masterbatch is in a range from 0.1% to 95.0% by weight, more preferably from 0.5% to 94% by weight, and more preferably still from 1% to 85% by weight, based in each case on the total weight of the masterbatch.

The amount of spherical metal particles and metal flakes in the masterbatch can therefore be very high. The amount may be suitably adjusted as a function of the plastic and of the desired final amount in the plastic.

The dispersion carrier may comprise at least one plastics component, waxes, resins, additives, solvents and/or plasticizers.

In the case of a masterbatch which is solid at room temperature (18-25° C.), the dispersion carrier preferably comprises plastics components, waxes, resins and/or additives.

A plastics component used in this context is preferably a polymer which is compatible with the plastics material into which it is to be incorporated. In accordance with one preferred version the plastics component used in the masterbatch of the invention is identical with the plastics material into which laser marking agent is to be incorporated.

Waxes used are preferably polyolefin degradation waxes or polyalkylene waxes, propylene waxes for example. A polypropylene wax which has proven very suitable is Licocene® from Clariant, Switzerland.

Preferred resins which can be used in the masterbatch of the invention are phenolic resins or ketonic resins such as, for example, Laropal A81 from BASF.

Additives which can be added to the laser marking agent include stabilizers, surfactants, defoamers, dispersants, corrosion inhibitors, such as organic phosphoric acids or phosphonic acids, for example, and/or surface-active substances, etc.

The additives may lead, for example, to an improvement in the ease of incorporation of the masterbatch into the plastic. The additives prevent agglomeration or sedimentation of the spherical metal particles and metal flakes in a masterbatch. The additives may be simply mixed together with the particles of the mixture of spherical metal particles and metal flakes, or the spherical metal particles and metal flakes of the mixture may in each case be coated, or have been coated, with the additives.

In accordance with one further preferred development of the invention the masterbatch includes an additive(s) content which is preferably in a range from 0.001% to 20% by weight, based on the total weight of the masterbatch. In accordance with a further preferred embodiment the additive(s) content is in a range from 0.01% to 10% by weight, more preferably in a range from 0.1% to 4% by weight, based in each case on the total weight of the masterbatch.

In the case of masterbatch which is liquid at room temperature (18-25° C.), the dispersion carrier preferably comprises solvents and/or plasticizers. A solvent used with particular preference is white oil. Plasticizers used are customarily phthalates, adipates, trimellitates, sebacates, tartaric acid derivatives, citric esters, polyesters, phosphates and/or fatty acid esters.

Preferred examples of these are bis-2-ethyloctyl phthalate, bis-2-ethylhexyl adipate, tri-2-ethylhexyl trimellitate or epoxidized soybean oil.

The masterbatch may comprise further components such as, for example, color pigments and/or dyes.

With regard to the concentration of the mixture of spherical metal particles and metal flakes in the masterbatch there are two preferred, different ranges distinguished:

In the case of the first preferred range, the amount of spherical metal particles and metal flakes in the masterbatch is preferably in a range from 80% to 99% by weight and more preferably from 85% to 95% by weight, based in each case on the total weight of the masterbatch. In this case it is preferred to add polymer-compatible solvents such as white oil and/or plastics components and also dispersants to the masterbatch.

The amount of the plastics components in the masterbatch in this case is preferably in a range from 0.5% to 20% by weight, more preferably from 1% to 15% by weight, and with particular preference from 2% to 10% by weight, based in each case on the total weight of the masterbatch.

In the second preferred case the composition of the masterbatch is already very similar to that of the laser-markable plastic, but the components are present in a more concentrated form.

The amount here of the mixture of spherical metal particles and metal flakes in the masterbatch is preferably in a range from 0.001% to 5% by weight and more preferably from 0.5% to 2% by weight, based in each case on the total weight of the masterbatch.

In the case of the second preferred case the masterbatch comprises predominantly plastics components.

The amount of the plastics component in the masterbatch in this case is preferably in a range from 50% to 99% by weight, more preferably from 60% to 98% by weight, and very preferably from 70% to 95% by weight, based in each case on the total weight of the masterbatch.

In this case the masterbatch is preferably either admixed to the plastic prior to extrusion or metered into the plastic in the course of extrusion.

Furthermore, a masterbatch of this kind generally comprises additives and optionally waxes, color pigments and/or dyes.

The masterbatch is produced, for example, in a suitable mixer, such as a tumbler mixer, for example. In this case the mixture of spherical metal particles and metal flakes and also, where appropriate, further components is combined with plastics pellets or plastics powder and/or plastics starting material in any presentation form, and the combined formulation is then extruded, for example. The masterbatch can also be produced by metering the mixture of the spherical metal particles and metal flakes and also, where appropriate, further components directly into the plastics melt in the course of extrusion.

Since in one preferred embodiment the laser marking agent or laser weldability agent for use in accordance with the invention contains relatively high fractions of spherical metal particles in comparison to metal flakes, the operation of mixing with plastic(s) may also take place under intensive conditions. Deformation of the spherical metal particles to platelets, corresponding to the metal flakes used, is observed only in the case of relatively coarse particles. The resulting mixture of plastic and the laser marking or laser weldability agent for use in accordance with the invention may then be subjected directly to further processing, as for example in an extruder or injection molding machine. After the desired plastics molding has been obtained, marking may be carried out by laser beam.

In view of the microscale size of the metal particles present in the mixture according to the invention it is preferred, for reasons not only of handling but also of health and safety, for the laser marking agent or laser weldability agent of the invention, or a masterbatch thereof, to be present in a low-dust or, preferably, non-dusting preparation.

Consequently, in a further-preferred form, the masterbatch comprising at least the laser marking agent or laser weldability agent and the plastics component(s), is in a compacted form. This compacted form comprises granules, tablets, briquettes, sausages or pellets. The solvent content of such compacted forms is 0.0% to 15% by weight and preferably 0.001% to 5% by weight, and more preferably 0.0% to less than 0.1% by weight, based in each case on the total weight of the compacted form. The size of the compacted forms in this case is in a range from 50 μm to 80 mm, preferably 200 μm to 50 mm, more preferably from 500 μm to 25 mm. One very suitable size of the compacted forms of the laser marking agent or laser weldability agent for use in accordance with the invention, or of the masterbatch, is situated in a range from 750 μm to 10 mm, preferably in the form of granules, tablets, briquets, sausages or pellets.

Compaction may be accomplished by here combining a mixture of spherical metal particles and metal flakes with the plastics component and, optionally, with a further binder, and subsequently carrying out granulation, pelletizing, tableting, extrusion, compressing, etc. Here, with introduction of heat, the plastics component is melted, and then joins with the spherical metal particles and metal flakes. After cooling, the form produced by the particular shaping operation is retained.

In a further embodiment the binder is dissolved in a suitable solvent and mixed with the laser marking agent or laser weldability agent and, where appropriate, other additives. In this embodiment subsequently, with stirring, the solvent is removed again under subatmospheric pressure and/or at elevated temperature. This produces three-dimensional granules of irregular shape. In another embodiment the paste is pelletized or tableted and then dried.

The aforementioned presentation forms allow a safe handling and incorporation into a plastic, without the danger of a metal dust explosion or adverse health effect.

Extremely advantageous in the case of the present invention is the fact that any clouding or graying of the plastic can be readily covered by addition of colorants. In the prior art, the brown or greenish colorations that occasionally occur are almost impossible to cover, since—in contrast to slight clouding or graying—they constitute a coloration.

In accordance with one further preferred embodiment of the invention, the metal particles present in the mixture according to the invention are provided with at least one inorganic metal oxide layer.

The at least one inorganic metal oxide layer may be applied separately to the metal particles. As a metal oxide layer it is possible, for example, to apply $SiO_2$ layer, $Al_2O_3$ layer or $TiO_2$ layer. It is also possible for combinations of metal oxide layers to be applied: for example, first $SiO_2$ and subsequently $TiO_2$, or first $TiO_2$ and subsequently $SiO_2$.

Coatings of this kind have no advantages in terms of laser markability but may be necessary if the plastic pigmented with the mixture according to the invention is exposed to corroding conditions. For example, animal tags may come into contact with the urine of the animals.

As a metal oxide layer it is preferred to apply an $SiO_2$ layer. The $SiO_2$ layer is preferably applied using sol-gel methods.

Starting compounds used for the $SiO_2$ layer are preferably tetraalkoxysilanes. Examples of these are as follows: tetramethoxysilane, tetraethoxysilane, tetrapropoxysilane, tetraisopropoxysilane or tetrabutoxysilane, or mixtures thereof.

The tetraalkoxysilane is first hydrolyzed in a preferably basic environment with addition of water, and subsequently an $SiO_2$ layer is deposited on the metal particles.

To catalyze the $SiO_2$ deposition it is preferred to add nitrogen-containing bases such as ammonia, alkylamines or dialkylamines. Suitable compounds are methylamine, ethylamine, dimethylamine, diethylamine, pyridine, piperazine, etc.

In accordance with a further preferred embodiment it is also possible for an organic-chemical surface modification to have been applied to the spherical metal particles and/or metal flakes. Between spherical metal particles and/or metal flakes and organic-chemical surface modification there may also be a metal oxide layer arranged, an $SiO_2$ layer, for example.

In one further variant the organic-chemical surface modification may be an organic-chemical polymer matrix that envelops the spherical metal particles and/or metal flakes. Such a matrix is applied preferably by targeted polymerization from monomers to the metal particles. An organic-chemical surface modification may bring about improved attachment to the plastic, as a result, for example, of the formation of a covalent bond between spherical metal particle and/or metal flake and the surrounding plastic.

The object on which the invention is based is further achieved by provision of a laser-markable and/or laser-weldable plastic which comprises a mixture with spherical metal particles and metal flakes that is intended for use as claimed in claims 1 to 11. Furthermore, the laser-markable and/or laser-weldable plastic may comprise a masterbatch of the invention as claimed in any of claims 12 to 15.

The laser-markable and/or laser-weldable plastic preferably comprises thermoplastic, thermoset or elastomeric plastics. Particular preference here is given to thermoplastics.

Suitable thermoplastic polymers include all of the thermoplastics that are known to a person skilled in the art. Suitable thermoplastic polymers are described in, for example, Kunststoff-Taschenbuch, Saechtling (Ed.), 25th edition, Hanser-Verlag, Munich, 1992, especially chapter 4 and references cited therein, and in Kunststoff-Handbuch, G. Becker and D. Braun (Eds.), volumes 1 to 11, Hanser-Verlag, Munich, 1966 to 1996.

Exemplary mention may be made as suitable thermoplastics of polyoxyalkylenes, polycarbonates (PC), polyesters such as polybutylene terephthalate (PBT) or polyethylene terephthalate (PET), polyolefins such as polyethylene or polypropylene (PP), poly(meth)acrylates, polyamides, vinylaromatic (co)polymers such as polystyrene, impact-modified polystyrene such as HI-PS, or ASA, ABS or AES polymers, polyarylene ethers such as polyphenylene ethers (PPE), polysulfones, polyurethanes, polylactides, halogen-containing polymers, polymers containing imide groups, cellulose esters, silicone polymers, and thermoplastic elastomers. Mixtures of different thermoplastics can also be used as materials for the plastics moldings. These mixtures may be single-phase or multiphase polymer blends.

The plastics to be inscribed or to be joined to one another may consist of identical or different thermoplastics and/or thermoplastic blends.

Polyoxyalkylene homopolymers or copolymers, especially (co)polyoxymethylenes (POM), and processes for preparing them are known per se to a person skilled in the art and are described in the literature. Suitable materials are available commercially under the brand name Ultraform® (BASF AG, Germany). Very generally these polymers contain at least 50 mol % of repeating —$CH_2O$— units in the main polymer chain. The homopolymers are generally prepared by polymerizing formaldehyde or trioxane, preferably in the presence of suitable catalysts. Polyoxymethylene copolymers and polyoxymethylene terpolymers are preferred. The preferred polyoxymethylene (co)polymers have melting points of at least 150° C. and molecular weights (weight average) M in the range from 5000 to 200 000, preferably from 7000 to 150 000 g/mol. Endgroup-stabilized polyoxymethylene polymers which have C—C bonds at the chain ends are particularly preferred.

Suitable polycarbonates are known per se and are obtainable, for example, in accordance with DE-B-1 300 266 by interfacial polycondensation or in accordance with DE-A-14 95 730 by reaction of biphenyl carbonate with bisphenols. A preferred bisphenol is 2,2-di(4-hydroxyphenyl)propane, referred to generally as bisphenol A. The relative viscosity of these polycarbonates is situated in general in the range from 1.1 to 1.5, in particular from 1.28 to 1.4 (measured at 25° C. in a 0.5% strength by weight solution in dichloromethane). Suitable polycarbonates are available commercially under the brand name Lexan® (GE Plastics, B.V., The Netherlands).

Suitable polyesters are likewise known per se and described in the literature. In their main chain they contain an aromatic ring which originates from an aromatic dicarboxylic acid. The aromatic ring may also be substituted, as for example by halogen such as chlorine and bromine or by $C_1$-$C_4$ alkyl groups such as methyl, ethyl, isopropyl and n-propyl, and n-butyl, isobutyl and/or tert-butyl groups. The polyesters can be prepared by reacting aromatic dicarboxylic acids, their esters or other ester-forming derivatives thereof with aliphatic dihydroxyl compounds in a manner known per se. Preferred dicarboxylic acids include naphthalenedicarboxylic acid, terephthalic acid, and isophthalic acid or mixtures thereof. Up to 10 mol % of the aromatic dicarboxylic acids may be replaced by aliphatic or cycloaliphatic dicarboxylic acids such as adipic acid, azelaic acid, sebacic acid, dodecanedioic acids, and cyclohexanedicarboxylic acids. Preference among the aliphatic dihydroxy compounds is given to diols having 2 to 6 carbon atoms, especially 1,2-ethanediol, 1,4-butanediol, 1,6-hexanediol, 1,4-hexanediol, 1,4-cyclohexanediol, and neopentyl glycol or mixtures thereof. Particularly preferred polyesters include polyalkylene terephthalates which derive from alkanediols having 2 to 6 C atoms. Of these, particular preference is given to polyethylene terephthalate (PET), polyethylene naphthalate, and polybutylene terephthalate (PBT). These products are available commercially, for example, under the brand names Rynite® (PET; DuPont, USA) and Ultradur® (PBT; BASF AG). The viscosity number of the polyesters is situated generally in the range from 60 to 200 ml/g (measured in a 0.5% strength by weight solution in a phenol/o-dichlorobenzene mixture (weight ratio 1:1 at 25° C.)).

Suitable polyolefins are, very generally, polyethylene and polypropylene and also copolymers based on ethylene or propylene, where appropriate also with higher α-olefins. Corresponding products are available, for example, under the trade names Lupolen® and Novolen®. The term "polyolefins" should also be taken to include ethylene-propylene elastomers and ethylene-propylene terpolymers.

Among the poly(meth)acrylates, mention may be made in particular of polymethyl methacrylate (PMMA) and also copolymers based on methyl methacrylate with up to 40% by weight of further copolymerizable monomers, such as n-butyl acrylate, tert-butyl acrylate or 2-ethylhexyl acrylate, such polymers being obtainable, for example, under the names Lucryl® (BASF AG) or Plexiglas® (Rohm GmbH, Germany). For the purposes of the invention, these also include impact-modified poly(meth)acrylates and also mixtures of poly(meth)acrylates and SAN polymers which have been impact-modified with polyacrylate rubbers (an example being the commercial product Terlux® from BASF AG).

Suitable polyamides are those with an aliphatic, partially crystalline or partially aromatic or amorphous construction, of any kind, and their blends, including polyetheramides such as polyether-block-amides. By polyamides are meant all known polyamides. Suitable polyamides generally have a viscosity number of 90 to 350 ml/g, preferably 110 to 240 ml/g (determined in a 0.5% strength by weight solution in 96% strength by weight sulfuric acid at 25° C. in accordance with ISO 307).

Semicrystalline or amorphous resins with a molecular weight (weight average) of at least 5000 g/mol, of the kind described, for example, in American U.S. Pat. Nos. 2,071,250, 2,071,251, 2,130,523, 2,130,948, 2,241,322, 2,312,966, 2,512,606, and 3,393,210, are preferred. Examples thereof are polyamides which derive from lactams having 7 to 13 ring members, such as polycaprolactam, polycapryllactam, and polylauryllactam, and also polyamides which are obtained from reacting dicarboxylic acids with diamines.

Dicarboxylic acids which can be used are alkanedicarboxylic acids having 6 to 12, more particularly 6 to 10, carbon atoms, and aromatic dicarboxylic acids. Mention may be made here of adipic acid, azelaic acid, sebacic acid, dodecanedioic acid (i.e., decanedicarboxylic acid) and/or isophthalic acid as acids.

Particularly suitable diamines are alkanediamines having 6 to 12, more particularly 6 to 8, carbon atoms and also m-xylylenediamine, di(4-aminophenyl)methane, di(4-aminocyclohexyl)methane, 2,2-di(4-aminophenyl)propane or 2,2-di(4-aminocyclohexyl)propane.

Preferred polyamides are polyhexamethyleneadipamide (PA66), e.g., the commercial product Ultramid® A (BASF AG), and polyhexamethylenesebacamide (PA 610), e.g., the commercial product Nylon® 610 (DuPont), polycaprolactam (PA 6), e.g., the commercial product Ultramid® B (BASF AG), and also copolyamides 6/66, in particular with a fraction of 5% to 95% by weight of caprolactam units, e.g., the commercial product Ultramid® C (BASF AG). PA 6, PA 66, and copolyamides 6/66 are particularly preferred.

Mention may also be made, moreover, of polyamides which are obtainable, for example, by condensation of 1,4-diaminobutane with adipic acid at elevated temperature (polyamide-4,6). Preparation processes for polyamides of this structure are described in, for example, EP-A 38 094, EPA 38 582, and EP-A 39 524.

Further examples are polyamides which are obtainable by copolymerizing two or more of the aforementioned monomers, or mixtures of two or more polyamides, the mixing ratio being arbitrary.

Moreover, partially aromatic copolyamides of this kind, such as PA 6/6T and PA 66/6T with a triamine content of less than 0.5%, preferably less than 0.3%, by weight (see EP-A 299 444) have proven particularly advantageous. The preparation of the low-triamine-content partially aromatic copolyamides may be accomplished in accordance with the processes described in EP-A 129 195 and 129 196.

Further suitable thermoplastic materials are vinylaromatic (co)polymers. The molecular weight of these polymers, which are known per se and are available commercially, is situated in general in the range from 1500 to 2 000 000, preferably in the range from 70 000 to 1 000 000 g/mol.

Merely by way of representation, mention may be made here of vinylaromatic (co)polymers of styrene, chlorostyrene, α-methylstyrene, and p-methylstyrene; in minor proportions, preferably not more than 20%, in particular not more than 8%, by weight, comonomers such as (meth)acrylonitrile or (meth)acrylic esters may also be involved in the construction. Particularly preferred vinylaromatic (co)monomers are polystyrene, styrene-acrylonitrile (SAN) copolymers, and impact-modified polystyrene (HIPS=high impact polystyrene). It is understood that mixtures of these polymers as well can be used. Preparation takes place preferably by the process described in EP-A-302 485.

Furthermore, ASA, ABS, and AES polymers (ASA=acrylonitrile-styrene-acrylic ester, ABS=acrylonitrile-butadiene-styrene, AES=acrylonitrile-EPDM rubber-styrene) are particularly preferred. These impact-tough, vinylaromatic polymers comprise at least one rubber-elastic graft polymer and a thermoplastic polymer (matrix polymer). Matrix material commonly employed is a styrene/acrylonitrile (SAN) polymer. It is preferred to use graft polymers which comprise as their rubber

- a diene rubber based on dienes, such as butadiene or isoprene, for example, (ABS);
- an alkyl acrylate rubber based on alkyl esters of acrylic acid, such as n-butyl acrylate and 2-ethylhexyl acrylate, (ASA);
- an EPDM rubber based on ethylene, propylene and a diene, (AES);

or mixtures of these rubbers and/or rubber monomers.

The preparation of suitable ABS polymers is described in depth in—for example—German patent application DE-A 19728629. For the preparation of ASA polymers, recourse may be made, for example, to EP-A 99 532. Details of the preparation of AES polymers are disclosed in, for example, U.S. Pat. No. 3,055,859 or U.S. Pat. No. 4,224,419. Reference is hereby made expressly to the patent specifications cited in this paragraph.

Polyarylene ethers are preferably polyarylene ethers per se, polyarylene ether sulfides, polyarylene ether sulfones or polyarylene ether ketones. Their arylene groups may be alike or different and independently of one another may denote an aromatic radical having 6 to 18 C atoms. Examples of suitable arylene radicals are phenylene, bisphenylene, terphenylene, 1,5-naphthylene, 1,6-naphthylene, 1,5-anthrylene, 9,10-anthrylene or 2,6-anthrylene. Of these, preference is given to 1,4-phenylene and 4,4'-biphenylene. Preferably these aromatic radicals are not substituted. However, they may carry one or more substituents. Suitable polyphenylene ethers are available commercially under the Noryl® designation (GE Plastics B.V., The Netherlands).

In general the polyarylene ethers have average molecular weights M (number average) in the range from 10 000 to 60 000 g/mol and viscosity numbers of 30 to 150 ml/g. Depending on the solubility of the polyarylene ethers, the viscosity numbers are measured either in 1% strength by weight N-methylpyrrolidone solution, in mixtures of phenol and o-dichlorobenzene, or in 96% strength sulfuric acid, in each case at 20° C. or 25° C.

The polyarylene ethers are known per se or can be prepared by methods that are known per se.

Preferred process conditions for the synthesis of polyarylene ether sulfones or polyarylene ether ketones are described in, for example, EP-A 113 112 and EP-A 135 130. Polarylene ether sulfones generally have a melting point of at least 320° C., polyarylene ether ketones one of at least 370° C. Suitable polyphenylene ether sulfones are available commercially, for example, under the Ultrason® E designation (BASF AG), suitable polyphenylene ether ketones under the Victrex® designation.

Furthermore, polyurethanes, polyisocyanurates, and polyureas are suitable materials for producing the plastics moldings. Soft, half-hard or hard, thermoplastic or crosslinked polyisocyanate polyaddition products, examples being polyurethanes, polyisocyanurates and/or polyureas, especially polyurethanes, are general knowledge and are available commercially under designations including that of Elastolan® (Elastogran GmbH, Germany). Their preparation is diversely described and is typically accomplished by reaction of isocyanates with isocyanate-reactive compounds under conditions which are general knowledge. The reaction is carried out preferably in the presence of catalysts and/or auxiliaries. When the products are foamed polyisocyanate polyaddition products, they are produced in the presence of customary blowing agents.

Suitable isocyanates include the aromatic, arylaliphatic, aliphatic and/or cycloaliphatic organic isocyanates that are known per se, preferably diisocyanates.

Isocyanate-reactive compounds which can be used include, for example, common-knowledge compounds having a molecular weight of 60 to 10 000 g/mol and a functionality with respect to isocyanates of 1 to 8, preferably 2 to 6 (in the case of thermoplastic polyurethanes, TPU, a functionality of about 2), examples being polyols having a molecular weight of 500 to 10 000 g/mol, e.g., polyether polyols, polyester polyols, polyether polyester polyols, and/or diols, triols and/or polyols having molecular weights of less than 500 g/mol.

Polylactides, in other words polymers of lactic acid, are known per se or can be prepared by processes that are known per se. Besides polylactide it is also possible to use copolymers or block copolymers based on lactic acid and further monomers. Usually linear polylactides are used. However, branched lactic acid polymers can be used as well. Serving as branching agents may be, for example, polyfunctional acids or alcohols.

Suitable halogen-containing polymers include, in particular, polymers of vinyl chloride, especially polyvinyl chloride (PVC) such as unplasticized PVC and plasticized PVC, and copolymers of vinyl chloride such as PVC-U molding compounds.

Additionally suitable are fluorine-containing polymers, especially polytetrafluoroethylene (PTFE), tetrafluoroethylene-perfluoropropylene copolymers (FEP), copolymers of tetrafluoroethylene with perfluoroalkyl vinyl ether, ethylene-tetrafluoroethylene copolymers (ETFE), polyvinylidene fluoride (PVDF), polyvinyl fluoride (PVF), polychlorotrifluoroethylene (PCTFE), and ethylene-chlorotrifluoroethylene copolymers (ECTFE).

Polymers containing imide groups are, in particular, polyimides, polyetherimides, and polyamidimides.

Suitable cellulose esters are for instance cellulose acetate, cellulose acetobutyrate, and cellulose propionate.

Also suitable in addition as thermoplastics are silicone polymers. Silicone rubbers in particular are suitable. These are customarily polyorganosiloxanes which have groups capable of crosslinking reactions. Polymers of this kind are described in, for example, Römpp Chemie Lexikon, CD-ROM version 1.0, Thieme Verlag Stuttgart 1995.

Finally it is also possible to employ the class of compound of the thermoplastic elastomers (TPE). TPE can be processed like thermoplastics but have rubber-elastic properties. TPE block polymers, TPE graft polymers, and segmented TPE copolymers comprising two or more monomer units are suitable. Particularly suitable TPE are thermoplastic polyurethane elastomers (TPE-U or TPU), styrene oligoblock copolymers (TPE-S) such as SBS (styrene-butadiene-styrene-oxy block copolymer) and SEES (styrene-ethylene-butylene-styrene block copolymer, obtainable by hydrogenating SBS), thermoplastic polyolefin elastomers (TPE-O), thermoplastic polyester elastomers (TPE-E), thermoplastic polyamide elastomers (TPE-A), and, in particular, thermoplastic vulcanisates (TPE-V). A person skilled in the art finds details on TPE in G. Holden et al., Thermoplastic Elastomers, 2nd edition, Hanser Verlag, Munich 1996.

The laser marking agent or laser weldability agent for use in accordance with the invention can be incorporated outstandingly into the aforementioned thermoplastics for the purpose, for example, of producing the masterbatch of the invention, or a plastic/laser marking agent mixture intended for direct further processing.

From a resultant plastic/laser marking agent mixture it is then possible, by thermal forming, to produce the desired shaped articles, examples being containers such as bottles, cups, trays, or films, etc.

The laser-markable and/or laser-weldable plastic of the invention can be produced by a process in which the above-described mixture with or of spherical metal particles and metal flakes is introduced into the plastics material. The amounts of the spherical metal particles and metal flakes introduced may be set as a function of plastics and/or intended use. The introduction of the spherical metal particles and metal flakes into the plastics material may take place in a customary mixer or else in an extruder in a conventional manner.

A method of producing the laser-markable and/or laser-weldable plastic, in which the mixture of spherical metal particles and metal flakes according to the invention is introduced into a plastics material, is likewise provided by the present invention.

In accordance with one preferred embodiment the fraction of the mixture according to the invention in the laser-markable and/or laser-weldable plastic is 0.0005% to 0.8% by weight, preferably 0.001% to 0.5% by weight, the amounts being based in each case on the total weight of the plastic.

Surprisingly the advantageous properties of the laser-markable and/or laser-weldable plastic of the invention can be achieved even with very low levels of laser marking agent. Below 0.0005% by weight of laser marking agent, the advantages according to the invention can be found no longer or only in a very restricted form.

It is preferred, moreover, for the fraction of the mixture of spherical metal particles and metal flakes in the plastic to be 0.005% to 0.5% by weight, even more preferably 0.01% to 0.2% by weight, based in each case on the total weight of the laser-markable plastic.

With regard to the metals used it has emerged that, at low concentrations, metal particles consisting of aluminum, silver, copper, zinc or iron in particular gave the best results. A further preferred embodiment therefore relates to plastics which comprise a mixture with or of spherical metal particles and metal flakes comprising these metals or alloys of these metals, preferably in concentrations of 0.0005% to 0.015% by weight, based on the total plastic.

The present invention allows plastics which can be given a high-contrast mark or inscription with a laser beam to be produced.

From an amount of 0.2% by weight upward, based on the total weight of the plastic, the material may become opaque. In an amount range between 0.05% by weight and 0.2% by weight, the first clouding may occur, and may rise as the concentration goes up to form a grayish coloration of the material. Above 0.8% by weight, the plastic is generally too opaque. Moreover, no further advantage in the quality of laser markability is perceptible. Consequently the use of more laser marking agent would only unnecessarily increase the production costs of the laser-markable plastic.

In an individual case, the amount of the mixture with or of spherical metal particles and metal flakes in the plastic may be adjusted in dependence on the layer thickness of the material to be marked; in this context, preferably, the amount of the mixture with or of spherical metal particles and metal flakes that is intended for use in accordance with the invention can be increased as the layer thickness of the plastic goes down.

The amount used of the mixture with or of spherical metal particles and metal flakes is dependent on the thickness and opacity of the plastic. The amount of the mixture with or of spherical metal particles and metal flakes in the plastic is preferably selected such that laser markability is good while at the same time the plastic is as highly transparent as possible. For instance, with relatively thick plastics, the amounts of the mixture with or of spherical metal particles and metal flakes added will tend to be lower, and will tend to be higher in the case of relatively thin plastics. Where the plastic is colored with further colorants, the graying due to the mixture with or of spherical metal particles and metal flakes will turn out to be relatively low, and higher amounts can be added. In each specific case, the optimum amount of the mixture with or of spherical metal particles and metal flakes that is to be used can be determined readily. In this context it is also necessary to take account of the nature of the laser used and also of the wavelength of the laser light.

In the case of relatively thin plastics, typically with a layer thickness of 50 to 250 µm, it is preferred to use 0.05% to 0.5% by weight of the mixture with or of spherical metal particles and metal flakes. In the case of thicker plastics, typically with a layer thickness of more than 250 µm up to 10 cm, it is preferred to use 0.0005% to 0.05% by weight of the mixture with or of spherical metal particles and metal flakes.

Hence the layer thickness of a film is customarily within a range from 20 µm to about 5 mm. The thickness of injection-molded plastics can amount up to about 6 cm.

In the case of a film it is possible to increase the amount of spherical metal particles and metal flakes in comparison to a plastics molding. In the case of a plastics molding, for example, it is possible to use an amount of 0.005% by weight of the mixture with or of spherical metal particles and metal flakes that is intended for use in accordance with the invention, whereas, in the case of a film, an amount of 0.02% by weight of the mixture with or of spherical metal particles and metal flakes that is intended for use in accordance with the invention may be suitable. The appropriate amount of the mixture with or of spherical metal particles and metal flakes may be determined readily by a person skilled in the art on the basis of experiments.

High-contrast marking of a plastic is possible—as will be shown in the examples—even with a concentration of inventive mixture of 0.001% by weight. These concentration figures in % by weight are based in each case on the total weight of the material and of the spherical metal particles and also metal flakes.

In the case of a layer thickness of the plastic in a range from 20 µm to 500 µm, the fraction of the mixture with or of spherical metal particles and metal flakes is situated preferably in a range from 0.005% to 0.2% by weight, more preferably from 0.02 to 0.05, based in each case on the total weight of plastic and spherical metal particles and also metal flakes.

In the case of a layer thickness of the plastic in the range from 500 µm to 2 mm, the fraction of the mixture with or of spherical metal particles and metal flakes is preferably in a range from 0.001% to 0.1% by weight, more preferably from 0.005 to 0.05, based in each case on the total weight of plastic and spherical metal particles and also metal flakes.

It has been found, entirely surprisingly, that—as will be shown in the examples—a plastic which comprises spherical metal particles and metal flakes with an amount in a range from 0.001% up to 0.05% by weight is completely transparent and at the same time can be marked outstandingly with a laser beam with high contrast. Preference is given to operating in a concentration range from 0.01% to 0.04% by weight of spherical metal particles and metal flakes.

The extremely small amount of laser marking agent to be used affords a number of advantages at once. Thus the materials properties of the plastics material are unaffected, or not substantially affected, by the addition of the laser marking agent of the invention.

In the case of the inventive use of a mixture with or of spherical metal particles and metal flakes in a range from 0.001% to 0.05% by weight in a transparent or clear plastics material, therefore, there is no deterioration, or no substantial deterioration, in the transparency and/or the color properties of the material doped with the laser marking agent of the present invention, and yet, surprisingly, high-contrast marking or identification with a laser beam is possible.

Furthermore, the present invention allows the extremely inexpensive provision of a plastics material, since the laser marking agent is produced from inexpensive materials and need only be added in a minor extent to the material to be marked. This is a key economic advantage of the present invention.

With these small amounts of added laser marking agent, the present invention differs greatly from other commercially employed agents such as, for example, Lazerflair® from Merck (Germany). Here, higher amounts are typically used, in the 0.1%-0.3% by weight range. At the same time, the plastic is also not substantially clouded, owing to the transparency of the pigment, but the use of large amounts is unadvantageous. Moreover, the presence of heavy metals in these pigments constitutes an unnecessary hazard.

For certain applications it is advantageous if the plastic of the invention contains essentially no pearlescent pigments. The disadvantages of pearlescent pigments in laser-markable plastics have already been stated earlier on above: pearlescent pigments can lead to a color change and to a pearl luster effect. In certain cases this is desired on decorative grounds; in many cases, however, the laser marking agent is intended not to influence the coloristic properties of the plastic—in other words, the laser marking agent must be transparent. The plastic itself is likewise to be colorlessly transparent or else to be given a monochrome coloration (e.g., blue, red, yellow, etc.). A decorative coloration through pearl luster is not desired in these cases.

The plastics of the invention ought therefore to contain pearlescent pigments at most in amounts in which they are still transparent in their effect and give rise practically to no flow lines. Accordingly the laser-markable and/or laser-weldable plastics of the invention can comprise pearlescent pigments in concentrations of 0% to 0.1% by weight, preferably of 0.0% to 0.05% by weight, based on the total plastic. The precise concentrations below which the deleterious properties of the pearlescent pigments are no longer observed are dependent of course on further parameters such as, in particular, the layer thickness of the plastic, but can be determined readily by a person skilled in the art.

With particular preference, laser-markable and/or laser-weldable plastics of the invention of this kind contain no pearlescent pigments. Preferably, therefore, no pearlescent pigments are used in the case of the present invention. Accordingly the masterbatch as well preferably contains no pearlescent pigments.

The laser-markable and/or laser-weldable plastics of the invention may further comprise customary adjuvants. These adjuvants may be selected, for example, from the group consisting of fillers, additives, plasticizers, lubricants or mold release agents, impact tougheners, color pigments, dyes, flame retardants, antistats, optical brighteners, antioxidants, antimicrobially active biostabilizers, chemical blowing agents or organic crosslinking agents, and also other adjuvants, or mixtures thereof.

Examples of fillers which can be used are as follows: $CaCO_3$ (e.g., Omya, Cologne; Ulmer Füllstoff Vertrieb), dolomite (e.g., Zieglar, Wunsiedel; Blancs Mineraux de Paris), $CaSO_4$ (US Gypsum, Chicago), silicates (Degussa, Frankfurt; Quarzwerke, Frechen), glass beads (Potter; GB; Owens Corning, Wiesbaden), talc (Norwegian Talc; Nordbayrische Farben- und Mineralwerke, Hof), kaolin (AKW, Hirschau; Luh, Walluf), mica (Norwegian Talc; Dorfner, Hirschau), feldspar (Omya, Paris), silicate beads (Langer, Ritterhude), silica (see silicates), $BaSO_4$ (Sachtleben, Duisburg, Scheruhn, Hof), $Al_2O_3$ or $Al(OH)_3$ (both: Martinswerk, Bergheim).

The additives may comprise, for example, dispersing additives, antioxidants, metal deactivators and/or light stabilizers and UV stabilizers.

Suitable antioxidants (heat stabilizers) are, for instance, sterically hindered phenols, hydroquinones, arylamines, phosphites, various substituted representatives of this group, and also mixtures thereof. They are available commercially for instance as Topanol® (ICI, London), Irgafos®, Irganox® (both Ciba-Geigy, Basel), Hostanox® (Clariant, Frankfurt) or Naugard® (Uniroyal, GB).

Examples of metal deactivators which can be used are as follows: carboxamides, hydrazones, hydrazines, melamine derivatives, benzotriazoles, phosphonic esters and/or thiazole derivatives.

Examples: Hostanox (Clariant, Frankfurt), Irganox (Ciba Geigy, Basel), Naugard (Uniroyal, GB).

Examples of light stabilizers and UV stabilizers which can be used are as follows: benzophenones, benzotriazoles, organic Ni compounds, salicylic esters, cyanocinnamic esters, benzylidenemalonates, benzoic esters, oxalanilides and/or sterically hindered amines, which may be monomeric and polymeric.

Examples: Chimasorb, Tinuvin (both Ciba-Geigy, Basel), Cyasorb (American Cyanamid), Hostavin (Clariant, Frankfurt), Uvinul (BASF, Ludwigshafen).

Examples of plasticizers which can be used are as follows: phthalic esters, phosphoric esters, adipic esters, azelaic esters, glutaric esters, sebacic esters, fatty acid esters, preferably oleates, stearates, rizinolates, laurates and/or octoates, with pentaerythritol, glycols, glycerol, etc., epoxidized fatty acid esters, citric esters, polyesters, benzoic esters, trimellitic esters, sulfonic esters, sulfamides, anilides, addition polymers, polycondensates, polyethylene glycols, abietic esters and/or derivatives, esters of acetic, propionic, butyric, ethylbutyric and/or ethylhexanoic acid.

Examples: Carbowax (DOW, Belgium), Cetamoll (BASF, Ludwigshafen), Edenol (Henkel, Dusseldorf), Elvaloy (DuPont de Nemours, USA), Lankroflex, (Lankro, GB), Palamoll, Palatinol (both BASF, Ludwigshafen).

Examples of lubricants which can be used are as follows: fatty alcohols, dicarboxylic esters, fatty acids of glycerol and of other short-chain alcohols, fatty acids, fatty acid amides, metal salts of fatty acids, oligomeric fatty acid esters, fatty alcohol-fatty acid esters, wax acids and their esters and soaps, polar polyethylene waxes and derivatives, apolar polyolefin waxes, natural and synthetic paraffins, silicone oils and/or fluoropolymers.

Examples: Licowax, Ceridust, Licolub, Licomont (all Clariant, Frankfurt), Irgawax (CibaGeigy, Basel), Loxiol (Henkel, Dusseldorf), Bärolub (Bärlocher, Munich).

Examples of impact modifiers which can be used are as follows: elastomers (EPM and EPDM), polyacrylates, polybutadiene, textile glass fibers, aramid fibers and/or carbon fibers.

The colorants may be inorganic pigments and/or organic pigments and/or organic dyes. However, essentially no pearl luster effect pigments are used.

Examples of flame retardants which can be used are as follows: suitable flame retardants are, for example, the halogen-containing compounds that are known to a person skilled in the art, alone or together with antimony trioxide, or phosphorus compounds, magnesium hydroxide, red phosphorus, and other common compounds or mixtures thereof. Known flame retardants include, for example, the phosphorus compounds disclosed in DE-A 196 326 75 or those disclosed in Encyclopedia of Chemical Technology, R. Kirk and D. Othmer (Eds.), vol. 10, 3rd edn., Wiley, New York, 1980, pages 340 to 420, such as phosphates, e.g., triaryl phosphates such as triscresyl phosphate, phosphites, e.g., triaryl phosphites or phosphonites. Phosphonites used are generally bis(2,4-di-tert-butylphenyl)phenyl-phosphonite, tris(2,4-di-tert-butylphenyl)phosphonite, tetrakis(2,4-di-tert-butyl-6-methylphenyl) 4,4'-biphenylylenediphosphonite, tetrakis(2,4-di-tert-butylphenyl) 4,4'-biphenylylenediphosphonite, tetrakis (2,4-dimethylphenyl) 1,4-phenylylenediphosphonite, tetrakis(2,4-di-tert-butylphenyl) 1,6-hexylylenediphosphonite and/or tetrakis(3,5-dimethyl-4-hydroxyphenyl) 4,4'-biphenylylenediphosphonite, tetrakis(3,5-di-tert-butyl-4-hydroxyphenyl) 4,4'-biphenylylenediphosphonite.

Examples: Fire Fighters (Great Lakes Chemicals), Fyrol (Dead Sea Bromine, Israel), Martinal (Martinswerk, Bergheim), Reofos (Ciba-Geigy, Basel), Phosflex (Akzo Chemicals, USA).

Examples of antistats which can be used are as follows: ethoxylated fatty amines, aliphatic sulfonates, quaternary ammonium compounds and/or polar fatty acid esters.

Examples: Bärostat (Bärlocher, Munich), Dehydat (Henkel, Dusseldorf), Hostastat (Clariant, Frankfurt), Irgastat (Ciba-Geigy, Basel).

Examples of optical brighteners which can be used are as follows: bisbenzotriazoles, phenylcoumarin derivatives, bis-styrylbiphenyls and/or pyrenetriazines, Examples: Hostalux (Clariant, Frankfurt), Uvitex (Ciba-Geigy, Basel).

Examples of antimicrobially active biostabilizers that can be used include the following: 10,10'-oxybisphenoxarsine, N-(trihalomethylthio)phthalimide, diphenylantimony 2-ethylhexanoate, Cu-8-hydroxyquinoline, tributyltin oxide and/or derivatives thereof Examples: Cunilate (Ventron, B), Preventol (Bayer, Leverkusen), Fungitrol (Tenneco, USA).

Examples of chemical blowing agents which can be used are as follows: azodicarbonamide and derivatives, hydrazine derivatives, semicarbazides, tetrazoles, benzoxazines and/or citric acid+$NaHCO_3$.

Examples: Hydrocerol 8 (Böhringer, Ingelheim), Porofor (Bayer, Leverkusen), Genitron (Schering, GB).

Examples of organic crosslinking agents which can be used are as follows: diaralkyl peroxides, alkyl aralkyl peroxides, dialkyl peroxides, tert-butyl peroxybenzoate, diacyl peroxides and/or peroxyketals.

Examples: Interox (Peroxidchemie, Höllriegelskreuth), Luperco, Luperox (Luperox, Günzburg).

In accordance with one preferred version of the present invention the laser-markable and/or laser-weldable plastic is a polymeric film or a label, preferably an adhesive label.

Products, including foods, are customarily wrapped with transparent polymeric films.

A polymeric film produced using the present invention thus permits contactless and unalterable inscription or identification. The inscribing or identifying of the polymeric film may take place both before and after wrapping of the product.

In one version of the present invention the plastic takes the form of a label, preferably an adhesive label. In the case of products which are provided not with a polymeric film but instead only with an adhesive label, the configuration of the plastic in the form of an adhesive label likewise affords the opportunity for inscription and/or identification of the labels using a laser beam.

In accordance with a further embodiment of the present invention the plastic is in the form of a three-dimensional plastics body, preferably a plastics container. On the plastics container it is possible to indicate, for example, the maximum keeping life of foods, chemicals, drugs, etc.

The three-dimensional plastics body may also take the form, for example, of a data medium such as a CD, DVD, CD-ROM, etc. On the basis of an abrasion-resistant and unalterable identification, it is possible to tell the original from counterfeits. The three-dimensional plastics body may also, for example, be a blister strip in which drugs are customarily sold in tablet or capsule form. For example, labels or plastics, especially plastics containers, can be provided with a bar code by laser beam.

In further embodiments according to the invention, the laser-markable and/or laser-weldable plastic may be a constituent of an article which itself need not be laser-markable and/or laser-weldable.

Inscription with a standard commercial laser is accomplished by introducing a sample body into the beam path of a laser. The marking obtained is determined by the irradiation time (or pulse number in the case of pulsed lasers) and irradiation output of the laser and also of the plastics system. The output of the lasers used is dependent on the particular application and may be readily determined in each individual case by a person skilled in the art.

Suitable in principle are all customary lasers, examples being gas lasers and solid-state lasers. Gas lasers are, for example (indicated in brackets is the typical wavelength of the radiation emitted): $CO_2$ lasers (10.6 µm), argon gas lasers (488 nm and 514.5 nm), helium-neon gas lasers (543 nm, 632.8 nm, 1150 nm), krypton gas lasers (330 to 360 nm, 420 to 800 nm), hydrogen gas lasers (2600 to 3000 nm), and nitrogen gas lasers (337 nm).

Solid-state lasers are, for example (in brackets the typical wavelength of the radiation emitted): Nd:YAG lasers ($Nd^{3+}$ $Y_3Al_5O_{12}$) (1064 nm) high-performance diode lasers (800 to 1000 nm), ruby lasers (694 nm), $F_2$ excimer lasers (157 nm), ArF excimer lasers (193 nm), KrCl excimer lasers (222 nm), KrF excimer lasers (248 nm), XeCl excimer lasers (308 nm), XeF excimer lasers (351 nm), and frequency-multiplied Nd:YAG lasers with wavelengths of 532 nm (frequency-doubled), 355 nm (frequency-tripled) or 266 nm (frequency-quadrupled).

Preferred lasers for laser inscribing are the Nd:YAG laser ($Nd^{3+}Y_3Al_5O_{12}$) (1064 nm).

Preferred for laser weldability is the Nd:YAG laser ($Nd^{3+}$ $Y_3Al_5O_{12}$) (1064 nm) and also the high-performance diode laser (800 to 1000 nm), both of which emit in the shortwave infrared.

The lasers used are operated typically at outputs of 1 to 400, preferably 5 to 100, and more particularly 10 to 50 watts.

The energy densities of the lasers used are situated in general in the range from 0.3 $mJ/cm^2$ to 50 $J/cm^2$, preferably 0.3 mJ/cm$^2$ to 10 J/cm$^2$. In the case of the use of pulsed lasers, the pulse frequency is generally in the range from 1 to 30 kHz. Corresponding lasers which can be used in the present context are available commercially.

One very great advantage of the laser marking agent of the invention is that the wavelength of the laser beam does not have to be set specifically for the spherical metal particles and metal flakes of the mixture. In contrast to metal oxides, metals have a broad absorption capacity, and this is why a very wide variety of lasers with different wavelengths can be used for laser marking a plastic doped with the laser marking material of the invention.

The prior art sometimes uses metal oxides such as antimony-doped tin oxide as absorber materials. Irrespective of the toxicological risks, these oxides require the use of a defined laser light wavelength in order to effect marking, which complicates handling.

The use of a plastic doped with the laser marking agent of the invention may be in all the fields where customary printing processes have to date been used to inscribe plastics. For example, shaped articles made from plastic doped with the laser marking agent of the invention may find application in the electrical, electronics, and automotive industries. The identification and inscription of, for example, cables, leads, trim strips, and functional parts in the heating, ventilation, and cooling segments, or switches, plugs, levers, and handles made of plastic doped with the laser marking agent of the invention, can be marked with the aid of laser light, even at places which are difficult to access.

Furthermore, plastics systems doped with the laser marking agent of the invention may be employed for packaging in the food segment or in the toy segment. Particular features of the marks on the packs are that they are wipe-resistant and scratch-resistant, are stable in the case of subsequent sterilization operations, and can be applied in a hygienically clean way in the marking operation.

A further important field of application for laser inscription is that of plastic tags for the individual identification of animals, known as cattle tags or ear tags. Via a barcode system, the information specific to the animal is stored. This information can be called up again on demand with the aid of a scanner. The inscription must be very durable, since the ear tags remain on the animals for several years in some cases. Laser-markable plastics comprise thermoplastics, thermosets, elastomers or rubber.

Laser-weldable plastics naturally always comprise thermoplastics.

In a further embodiment, the laser marking agents are used in plastics for subsurface laser engraving for the generation of two- or three-dimensional image structures. Subsurface laser engraving processes are described in DE 10 2005 011 180 A1, for example. A mixture of spherical metal powders and metal flakes, which are particularly suitable for these purposes, comprise a particle size distribution used with a $D_{90}$ value of less than 20 μm. In the case of these spherical metal particles the $D_{50}$ value of the particle size distribution is preferably less than 11 μm; in the case of the metal flakes, the $D_{50}$ value of the particle size distribution is preferably <10 μm.

EXAMPLES

The present invention is illustrated with reference to the examples below, though without being restricted thereto.

Inventive Example 1

A mixture of spherical aluminum particles (ECKART GmbH, Fürth, Germany) having a $D_{particle, 50}$ value of 1.6 μm, a $D_{particle, 90}$ value of 3.4 μm (determined by means of laser granulometry using a Helos instrument from Sympatec, Germany), and aluminum flakes (Chromal XV, ECKART GmbH, Fürth, Germany) having a $D_{flake, 50}$ value of 5.0 μm was processed with thermoplastic polypropylene (PP) (R 771-10; DOW, Germany, Wesseling) by injection molding to form plates (area 42×60 mm, thickness 2 mm).

To prepare a 1.0% by weight mixture, the procedure used was as follows:

495 g of polypropylene pellets and 5 g of a mixture of spherical aluminum particles and powderous aluminum flakes (consisting of 95% by weight spherical particles and 5% by weight flakes) with a $D_{mixture, 50}$ value of 2.5 μm and a $D_{mixture, 90}$ value of 10.5 μm were mixed in a tumble mixer and then processed to pellets in a twin-screw extruder (Bersdorff, Germany, diameter 25 mm, 28 L/D) without addition of further additives at a processing temperature of about 230° C. These pellets were subsequently processed using an injection molding machine (Arburg Allrounder 221-55-250) at the particular processing temperature specific to the material (e.g., PP 260° C.) to give the specimen plaques having the dimensions specified above.

In an analogous procedure, concentration series were produced in polypropylene with addition of in each case 1.0%, 0.5%, 0.2%, 0.1%, 0.05%, 0.02%, 0.01%, 0.005%, and 0.002% by weight of the mixture of spherical aluminum particles and aluminum flakes (consisting of 95% by weight spherical particles and 5% by weight flakes), the weight figure referring in each case to the total weight of polypropylene and spherical aluminum particles and also aluminum flakes, and the plaques obtained in each case were inscribed using an Nd:YAG laser (wavelength: 1064 nm; output: 8 W, pulse frequency: 5 KHz; write speeds: 50-350 mm/s). The figures in % by weight are based in each case on the total weight of aluminum particles and PP.

When a mixture of spherical aluminum particles and aluminum flakes (consisting of 95% by weight spherical particles and 5% by weight flakes) was used, it was possible, above an amount of 0.002% by weight relative to PP, to obtain high-contrast, dark and abrasion-resistant marks which exhibited excellent edge definition and dot precision. The PP plates remained transparent and color-neutral.

In the case of an amount of a mixture of spherical aluminum particles and aluminum flakes in a range of 0.05-0.2% by weight, increasingly a grayish coloration was found, which accompanied a loss of transparency. PP plates with a spherical aluminum particles and aluminum flakes content of more than 0.2% by weight were gray-opaque.

No disruptive coarse particles or shards at all were observed. Moreover, even at low concentration ranges (0.005-0.02% by weight), with relatively high write speeds (250-350 mm/s, 8 W, pulse frequency: 5 KHz) of the laser, excellent dot precisions and high contrasts were ensured.

Comparative Example 2

As a comparative example, PP plates were processed by injection molding in the same way as in example 1, without addition of a mixture of spherical aluminum particles and aluminum flakes, and were treated with an Nd:YAG laser.

The resulting PP plates were practically impossible to mark with the laser.

Comparative Example 3

Spherical aluminum particles (ECKART) having a $D_{particle, 50}$ value of 39.3 μm and a $D_{particle, 90}$ value of 69.1 μm (determined with the Helos instrument as in example 1) were processed with polypropylene (PP) in accordance with example 1.

At quantities in a range of 0.005-0.1% by weight of spherical aluminum particles in PP, based in each case on the total weight of PP and spherical aluminum particles, it was possible to obtain high-contrast, dark and abrasion-resistant marks which exhibited good dot precision.

The contrast and the edge definition were already significantly reduced by comparison to example 1.

The PP plates remained transparent and color-neutral. At quantities in a range of 0.1-1.0% by weight of spherical aluminum particles, increasingly a grayish coloration was found, which accompanied a loss of transparency. PP plates with a spherical aluminum particle content of more than 1.0% by weight were gray-opaque.

Over the entire concentration range, optically disruptive coarse particles were observed, whose influence on the visual appearance became increasingly more significant as the concentration went up.

Comparative Example 4

Fine aluminum flakes (PC 200, Eckart GmbH, Fürth, Germany) having a $D_{flake, 50}$ value of 4.0 µm and a $D_{flake, 90}$ value of 10.0 µm (determined with the Helos instrument as in example 1) were processed with polypropylene in the same way as in example 1.

On addition of ≥0.005% by weight of aluminum flakes, markings were obtainable. In this case the PP plates had a gray clouding even at this level of aluminum flakes. In the case of an amount of 0.01% by weight of aluminum flakes, the gray clouding was comparable with the gray clouding obtained in example 1 for a level of ≥0.1% by weight. The plates were gray-opaque even for a pigment content of only 0.02% by weight of aluminum flakes. Consequently the unwanted clouding behavior is significantly higher than in the case of the pigment mixture set out in example 1.

The markings were high-contrast, dark and abrasion-resistant, but exhibited reduced dot precision as compared with example 1. Moreover, the typical flow lines and streaks that occur in the plastics material as a result of injection molding when platelet-shaped aluminum flakes are used exclusively were significantly observable.

Inventive Example 5

A mixture of spherical aluminum particles (ECKART GmbH, Fürth, Germany, having a $D_{particle, 50}$ value of 1.6 µm and a $D_{particle, 90}$ value of 3.4 µm (determined by means of laser granulometry using a Helos instrument from Sympatec, Germany) and aluminum flakes (Chromal XV, ECKART, GmbH, Fürth, Germany) having a $D_{flake, 50}$ value of 5.0 µm was processed in the same way as in example 1 in mixing ratios (weight fractions) of in each case 500:1, 200:1, 100:5, 50:1, 30:1, 20:1, 10:1, 5:1, 3:1, 2:1, and 1:1, with a constant concentration of 0.02% by weight of the pigment mixture in polypropylene.

Over the mixing range of spherical aluminum particles to aluminum flakes of 500:1 to 10:1, it was possible to obtain very high-contrast marks with excellent dot precisions, with retention of the transparency, even at heightened write speeds (350 mm/s). At a mixing ratio of 10:1 to 1:1, increasing clouding was observed. Only at a mixing ratio of 1:1 did the plates become gray-opaque.

Inventive Example 6

A mixture of spherical aluminum particles (ECKART GmbH, Fürth, Germany), having a $D_{particle, 50}$ value of 1.6 µm and a $D_{particle, 90}$ value of 3.4 µm and aluminum flakes (Chromal I, ECKART, GmbH, Fürth, Germany) having a $D_{flake, 50}$ value of 30.5 µm was processed in the same way as in example 5 in different mixing ratios (weight fractions) of in each case 500:1, 200:1, 100:5, 50:1, 30:1, 20:1, 10:1, 5:1, 3:1, 2:1, and 1:1, with a constant concentration of 0.02% by weight in PP.

Over the mixing range of spherical aluminum particles to aluminum flakes of 500:1 to 10:1, it was possible to obtain very high-contrast marks with excellent dot precisions, with retention of the transparency, even at heightened write speeds (350 mm/s). At a mixing ratio of 1:1, there was some decrease in the dot precision, and, moreover, clouding and the incidence of coarse particles were observed.

Comparative Example 7

Mica flakes with antimony-doped tin oxide coating (Lazerflair® 825, E. Merck KGaA, Germany) were processed with PP in accordance with example 1.

The PP plates showed properties comparable with those of the PP plates obtained in example 1. Here, however, the dot precisions observed over all concentration ranges, although good, were reduced by comparison with those of the inventive examples. A first clouding occurred at concentrations of ≥0.1% by weight, and the PP plates became opaque at concentrations of ≥2.0% by weight. Instead of a gray coloration obtained in the inventive examples with an aluminum particle content of ≥0.1% by weight, in the case of the Laserflair® 825 pigments a greenish coloration occurred in an analogous way. The Laserflair® 825 pigment contains toxic antimony.

Comparative Example 8 (Along the Lines of EP 1 145 864 A1)

In the same way as in example 1, a silver pearlescent pigment (PX1001, ECKART) was processed in polypropylene (PP) in a concentration of 0.49% by weight. In this case it was possible to obtain high-contrast, dark and abrasion-resistant marks which exhibited satisfactory to adequate edge definition and dot precision. However, in this case the PP plates had a pearly light-luster and were opaque.

Comparative Example 9: (Along the Lines of EP 1 145 864 A1)

In the same way as in example 1, a silver pearlescent pigment (PX1001, ECKART) was processed in polypropylene (PP), in a concentration of 0.49% by weight, along with zinc powder which had a particle size distribution as follows: $D_{10}$=1.9 µm; $D_{50}$=3.4 µm; $D_{90}$=6 µ(zinc dust 17640, manufacturer: Norzinko GmbH, Gosslar, Germany) in 0.0098% by weight with PP.

The results corresponded exactly to those given under comparative example 8.

Comparative Example 10

In the same way as in example 1, zinc powder (zinc dust 17640, Norzinko GmbH, Gosslar, Germany) was processed with polypropylene (PP).

When the zinc powder was used at an amount above 0.005% relative to PP, it was possible to obtain high-contrast, dark and abrasion-resistant marks which exhibited satisfactory edge definition and dot precision. At levels added of 0.05% by weight of more, very good dot precisions and edge definitions were obtained. The PP plates remained transparent and color-neutral.

At a level of zinc powder of 0.05% by weight and above, a grayish coloration was increasingly observed, which went hand in hand with a loss of transparency. PP plates with a zinc powder content of more than 1.0% by weight were gray-opaque. However, good markings were achievable only at relatively low write speeds of the Nd:YAG laser (50 mm/s, 8 W, pulse frequency: 5 KHz) with very good dot precision and high contrast.

Comparative Example 11

In the same way as in example 1, a silver pearlescent pigment (PX1001, ECKART) was processed in a concentration of 0.05% by weight, along with zinc powder (zinc dust 17640, Norzinko GmbH, Gosslar, Germany) in a concentration of 0.05% by weight, with PP.

The results were comparable with those set out in example 10, but in this case somewhat reduced dot precisions were observed. The plates remained transparent at the stated concentrations.

From the examples above it can be summarized that the present invention allows the provision of laser-markable plastics which can be marked with a laser transparently and at the same time with very high contrast and high distinctness of image and using small amounts of laser marking agent.

A very high-contrast mark is generally obtainable at a level of a mixture of spherical metal particles and metal flakes of 0.002% by weight or above, based on the total weight of the plastics composition and of the spherical metal particles and also the metal flakes. Gray coloration or clouding occurs in general above a level of spherical metal particles and metal flakes—in each case of aluminum in the case of the examples—of 0.05% by weight.

From comparative example 2 it is evident that, without the use of a laser marking agent, a plastic (in this case polypropylene) is practically impossible or is difficult to mark.

From comparative example 3 it is evident that spherical metal powders do allow laser markability, but the dot precisions, distinctness of image, and efficiency are reduced in comparison to the inventive mixture.

Comparative example 4 shows that the exclusive use of metal flakes leads to severe clouding and opacity even at very low concentrations.

Inventive examples 5 and 6 underscore the advantages of the preferred embodiments in which, in particular, fine metal particles are used.

Comparative example 7 shows good results for laser marking, but using laser marking agents which contain toxic antimony.

From comparative examples 8 to 9 it is evident that using mixtures of metal powders and pearlescent pigments as laser marking agents results in reduced dot precision and in unwanted colorations and/or luster effects.

The results of comparative examples 10 and 11, relative to those of comparative examples 8 and 9, show clearly the advantages associated with use of metal particles without or with only small amounts of pearlescent pigments. The marking results are equivalent, but without coloration of the matrix. The addition of pearlescent pigments to metal powders, accordingly, is not advantageous.

Inventive examples 12 and 14 and also comparative examples 13 and 15 below highlight the particular suitability of the mixture of spherical metal particles and metal flakes as a laser weldability agent.

Examples Relating to Laser Weldability

Inventive Example 12

A mixture of spherical aluminum particles (ECKART GmbH, Fürth, Germany) having a $D_{particle,\ 50}$ value of 1.6 µm and a $D_{particle,\ 90}$ value of 3.4 µm (determined by means of laser granulometry using a Helos instrument from Sympatec, Germany) and aluminum flakes (Chromal XV, ECKART GmbH, Fürth, Germany) having a $D_{flake,\ 50}$ value of 5.0 µm (mixture consisting of 95% by weight spherical particles and 5% by weight flakes, weight ratio 19:1, $D_{mixture,\ 50}$ value of 2.5 µm, $D_{mixture,\ 90}$ value of 10.5 µm) were processed with a fraction of 0.05% by weight with thermoplastic polypropylene (R 771-10; DOW, USA) to plates in an injection molding process (in analogy to example 1, area 42×60 mm, thickness 1 mm).

A plate thus obtained was covered with a corresponding plate, without addition of spherical aluminum particles and aluminum flakes, made of thermoplastic polypropylene (R 771-10; DOW, USA) and a 10×10 mm area was irradiated using an Nd:YAG laser (1064 nm; 8 W, pulse frequency 5 KHz; write speed 50 mm/s). As a result it was possible to induce melting of the plates at their area of contact in the irradiated region. The weld could be separated again only by employing force.

Comparative Example 13

In the same way as in example 12, the procedure was carried out with two plates, without addition of spherical aluminum particles and aluminum flakes, made from thermoplastic polypropylene (R 771-10; DOW, USA). However, it was not possible to induce melting of the plastics plates.

Inventive Example 14

A mixture of spherical aluminum particles (ECKART GmbH, Fürth, Germany) having a $D_{particle,\ 50}$ value of 1.6 µm, a $D_{particle,\ 90}$ value of 3.4 µm (determined by means of laser granulometry using a Helos instrument from Sympatec, Germany) and aluminum flakes (Chromal XV, ECKART GmbH, Fürth, Germany) having a $D_{flake,\ 50}$ value of 5.0 µm (mixture consisting of 95% by weight spherical particles and 5% by weight flakes, weight ratio 19:1, $D_{mixture,\ 50}$ value of 2.5 µm, $D_{mixture,\ 90}$ value of 10.5 µm) was processed with a fraction of 0.5% by weight with low-density polyethylene (LDPE) (LDPE 410-E, DOW, USA) to blown films having a thickness of 100 µm by means of a film extruder (type: Scientific, LabTech, Thailand). A film section (110×70 mm) was covered with a corresponding LDPE film, without addition of spherical aluminum particles and aluminum flakes, and treated in the same way as in example 20. As a result of this it was possible to induce melting of the films at their contact area in the irradiated region. The weld could be separated again only with application of force and with destruction of the films at the site of melt fusion.

ComparativE Example 15

The procedure of example 14 was repeated with two unpigmented films of low-density polyethylene (LDPE) (LDPE 410-E, DOW, USA). However, it was not possible to induce melt fusion of the polymeric films.

What is claimed is:

1. A plastic that is at least one of laser-markable and laser-weldable, wherein the plastic comprises a) a mixture with spherical metal particles and metal flakes or b) a masterbatch comprising the mixture with spherical metal particles and metal flakes and at least one dispersion carrier, and wherein the particle size distribution of the spherical metal particles and metal flakes in the mixture, as determined by means of laser granulometry, in the form of the volume-averaged cumulative undersize particle size distribution, has a $D_{mixture, 90}$ value of <100 μm and a $D_{mixture, 50}$ <60 μm.

2. The plastic as claimed in claim 1, wherein the fraction of the spherical metal particles and the metal flakes in the plastic is in a range from 0.0005% to 0.8 by weight, based on the total weight of the plastic.

3. The plastic as claimed in claim 2, wherein the fraction of the spherical metal particles and the metal flakes in the plastic is in a range from 0.001% to 0.5% by weight, based on the total weight of the plastic.

4. The plastic as claimed in claim 1, wherein the fraction of the spherical metal particles and the metal flakes in the plastic is in a range from 0.005% to 0.5% by weight, based on the total weight of the plastic.

5. The plastic as claimed in claim 4, wherein the fraction of the spherical metal particles and the metal flakes in the plastic is in a range from 0.01% to 0.1% by weight, based on the total weight of the plastic.

6. The plastic as claimed in claim 1, wherein the plastic is a plastic film or a plastic label.

7. The plastic as claimed in claim 6, wherein the plastic comprises the plastic film having a fraction of spherical metal particles and the metal flakes in a range from 0.01% to 1.0% by weight, based on the total weight of the plastic film.

8. The plastic as claimed in claim 7, wherein the fraction of the spherical metal particles and the metal flakes is in a range from 0.02% to 0.5% by weight, based on the total weight of the plastic film.

9. The plastic as claimed in claim 1, wherein the plastic is a three-dimensional plastic body.

10. The plastic as claimed in claim 1, wherein the plastic is a constituent of an article which itself is not, respectively, laser-markable or laser-weldable.

11. The laser-markable plastic as claimed in claim 1, wherein the plastic comprises a thermoplastic, thermoset, elastomer or rubber.

12. The laser-weldable plastic as claimed in claim 1, wherein the plastic comprises a thermoplastic.

* * * * *